United States Patent
Wang et al.

(10) Patent No.: US 12,159,706 B2
(45) Date of Patent: Dec. 3, 2024

(54) IMAGE-DRIVEN BRAIN ATLAS CONSTRUCTION METHOD, DEVICE AND STORAGE MEDIUM

(71) Applicant: SHENZHEN INSTITUTES OF ADVANCED TECHNOLOGY, Guangdong (CN)

(72) Inventors: Shuqiang Wang, Guangdong (CN); Junren Pan, Guangdong (CN); Yanyan Shen, Guangdong (CN)

(73) Assignee: SHENZHEN INSTITUTES OF ADVANCED TECHNOLOGY, Guangdong (CN)

( * ) Notice: Subject to any disclaimer, the term of this patent is extended or adjusted under 35 U.S.C. 154(b) by 0 days.

(21) Appl. No.: 17/764,755

(22) PCT Filed: Feb. 7, 2021

(86) PCT No.: PCT/CN2021/075798
§ 371 (c)(1),
(2) Date: Mar. 29, 2022

(87) PCT Pub. No.: WO2022/147885
PCT Pub. Date: Jul. 14, 2022

(65) Prior Publication Data
US 2024/0029866 A1    Jan. 25, 2024

(30) Foreign Application Priority Data

Jan. 9, 2021 (CN) .......................... 202110026745.5

(51) Int. Cl.
   *G16H 30/00*       (2018.01)
   *G06T 7/00*        (2017.01)
   (Continued)

(52) U.S. Cl.
CPC ........... *G16H 30/40* (2018.01); *G06T 7/0012* (2013.01); *G16H 50/20* (2018.01);
(Continued)

(58) Field of Classification Search
CPC ........ G16H 30/40; G16H 50/20; G16H 30/20; G16H 50/70; G06T 7/0012;
(Continued)

(56) References Cited

U.S. PATENT DOCUMENTS

2016/0300352 A1* 10/2016 Raj .................... G06V 10/764
2021/0256368 A1* 8/2021 Payne ...................... G06N 3/04
(Continued)

FOREIGN PATENT DOCUMENTS

CN         103093087 A      5/2013
CN         104715260 A      6/2015
(Continued)

OTHER PUBLICATIONS

Xiao L. et al., Multi-Hypergraph Learning Based Brain Functional Connectivity Analysis in fMRI Data, IEEE Trans Med Imaging, May 2020.
(Continued)

*Primary Examiner* — Md K Talukder
(74) *Attorney, Agent, or Firm* — Brooks Kushman P.C.

(57) ABSTRACT

The present application provides an image-driven brain atlas construction method and apparatus, a device and a storage medium, and involves in the field of medical imaging technologies. The method includes: acquiring a node feature matrix, where the node feature matrix includes time sequences of multiple nodes of a brain; performing hypergraph data structure transformation on the node feature matrix to acquire a first hypergraph incidence matrix; inputting the first hypergraph incidence matrix and the node feature matrix into a trained hypergraph transition matrix (Continued)

generator for processing to output and acquire a first hypergraph transition matrix, where the first hypergraph transition matrix characterizes a constructed multi-modal brain atlas. The technical solution provided by the present application can construct the multi-modal brain atlas, and this multi-modal brain connection structure can express more feature information. When it is applied to the brain disease diagnosis process, the accuracy of disease diagnosis can be improved.

15 Claims, 3 Drawing Sheets

(51) Int. Cl.
    *G16H 30/40*     (2018.01)
    *G16H 50/20*     (2018.01)

(52) U.S. Cl.
    CPC ............... *G06T 2207/20081* (2013.01); *G06T 2207/20084* (2013.01); *G06T 2207/30016* (2013.01)

(58) Field of Classification Search
    CPC . G06T 2207/20081; G06T 2207/20084; G06T 2207/30016; Y02D 10/00; G06N 3/08
    See application file for complete search history.

(56) References Cited

U.S. PATENT DOCUMENTS

2022/0309155 A1*   9/2022   Payne .................. G06N 3/0464
2024/0029866 A1*   1/2024   Wang .................... G16H 50/70

FOREIGN PATENT DOCUMENTS

CN         106203470 A     12/2016
CN         107658018 A     2/2018

OTHER PUBLICATIONS

Su L., Vertex-Weighted Hypergraph Learning for Multi-View Object Classification, Proceedings of the Twenty-Sixth International Joint Conference on Artificial Intelligence, Aug. 2017.

Zhu Y., et al., Dynamic Hyper-Graph Inference Framework for Computer-Assisted Diagnosis of Neurodegenerative Diseases IEEE Transactions on Medical Imaging, May 2019.

Zhzng Z., et al., Dynamic Hypergraph Structure Learning Proceedings of the 27th International Joint Conference on Artificial Intelligence, Jul. 2018.

* cited by examiner

IMAGE-DRIVEN BRAIN ATLAS CONSTRUCTION METHOD, DEVICE AND STORAGE MEDIUM

CROSS-REFERENCE TO RELATED APPLICATIONS

The present application is a national stage of International Application No.: PCT/CN2021/075798 filed on Feb. 7, 2021 and claims priority of Chinese Patent Application No. 202110026745.5 on Jan. 9, 2021, the contents each of which are incorporated herein by reference thereto in their entity.

TECHNICAL FIELD

The present application involves in the field of medical imaging technologies, and particularly relates to an image-driven brain atlas construction method, a device and a storage medium.

BACKGROUND

With the development of medical imaging technologies, different brain atlases can be generated based on image data collected in different modalities. For example, through collecting DTI (Diffusion Tensor Imaging) data, a structural connection matrix (including density of fiber tracts between various brain regions of a brain, and also known as a structural connection atlas) can be generated, which can express histological and anatomical information of the brain. Trough collecting rs-fMRI (resting-state functional Magnetic Resonance Imaging) data of the brain, a node feature matrix (including temporal feature sequences of the various brain regions, and also known as a functional connection atlas) is generated, which can express functional connection information between the various brain regions. The brain atlas is a very important reference in the process of diagnosing brain diseases.

However, most of the current brain atlases are generated based on single-modality image data, which can express less feature information. Therefore, it may lead to inability to extract effective disease information from the brain atlas, resulting in misjudgment of disease diagnosis.

SUMMARY

Given this, embodiments of the present application provide an image-driven brain atlas construction method, an image-driven brain atlas construction apparatus, a device and a storage medium, which can solve the problem that the current brain atlases can express less feature information.

In order to implement the above purpose, in a first aspect, an embodiment of the present application provides an image-driven brain atlas construction method, which includes: acquiring a node feature matrix, where the node feature matrix comprises time sequences of multiple nodes of a brain; performing hypergraph data structure transformation on the node feature matrix to acquire a first hypergraph incidence matrix; inputting the first hypergraph incidence matrix and the node feature matrix into a trained hypergraph transition matrix generator for processing to output and acquire a first hypergraph transition matrix, where the first hypergraph transition matrix characterizes a constructed multi-modal brain atlas.

When the construction method provided by the present application is used, the multi-modal brain atlas can be constructed through transforming the node feature matrix into the hypergraph data structure and calculating the first hypergraph transition matrix. Compared with the current brain connection structure generated based on single-modal image data, this multi-modal brain connection structure can express more feature information. When it is applied to a brain disease diagnosis process, the accuracy of disease diagnosis can be improved.

Optionally, the performing hypergraph data structure transformation on the node feature matrix to acquire the first hypergraph incidence matrix includes: transforming the node feature matrix into first hypergraph data by using a Guth-Katz polynomial clustering algorithm; transforming the node feature matrix into second hypergraph data by using a KNN algorithm; fusing the first hypergraph data and the second hypergraph data to acquire the first hypergraph incidence matrix.

Based on this optional implementation, through constructing the first hypergraph data by using the Guth-Katz polynomial clustering algorithm, and then fusing the first hypergraph data with the second hypergraph data to acquire the first hypergraph incidence matrix, topological information between the nodes in the node feature matrix can be better preserved, and at the same time redundant interference information is effectively eliminated, thereby the accuracy of the first hypergraph incidence matrix is improved.

Optionally, the processing of the node feature matrix by the hypergraph transition matrix generator includes: performing several iterative calculations based on the first hypergraph incidence matrix and the node feature matrix to obtain a target hyperedge feature matrix and a target node feature matrix; determining a node weight matrix according to the first hypergraph incidence matrix and the target node feature matrix; determining a hyperedge weight matrix according to the target hyperedge feature matrix; determining the first hypergraph transition matrix according to the hyperedge weight matrix and the node weight matrix.

Based on this optional implementation, several times of iterative calculations are performed through the first hypergraph incidence matrix and the node feature matrix to acquire the target hyperedge feature matrix and the target node feature matrix. By using this kind of hypergraph edge neuron algorithm, complementary information and potential connections between different modal data can be fully mined, and unnecessary parameters can be reduced, thereby avoiding model overfitting and providing strong generalization ability, which is more suitable for learning small scale of samples.

Optionally, each of training samples in a training set is preprocessed to acquire a node feature matrix sample and a structural connection matrix sample; hypergraph data structure transformation is performed on the node feature matrix sample to acquire a second hypergraph incidence matrix; the second hypergraph incidence matrix and the node feature matrix sample are input into an initial hypergraph transition matrix generator for processing to output and acquire a second hypergraph transition matrix; based on a random walk principle on a hypergraph, an incidence node set $N_{real}(v)$ acquired based on the structural connection matrix sample and an incidence node set $N_{fake}(v)$ acquired based on the second hypergraph transition matrix for each of the nodes corresponding to the training samples are determined; discrimination is performed on the incidence node set $N_{real}(v)$ and the incidence node set $N_{fake}(v)$ of each of the nodes by using a discriminator to acquire discrimination results corresponding to the training samples;

iterative training is performed according to the discrimination result corresponding to each of the training samples and a preset loss function to acquire the hypergraph transition matrix generator.

Based on this optional implementation, the kernel function transformation and the Lagrange multiplier method in the traditional training method is replaced by using the random walk principle on the hypergraph, such that the complicated calculation in the non-convex optimization problem and the problem that the loss function can not stably converge toward the global optimal point are avoided, thereby the robustness of the model as well as the training efficiency are improved.

Optionally, the performing discrimination on the incidence node set $N_{real}(v)$ and the incidence node set $N_{fake}(v)$ of each of the nodes by using a discriminator to acquire discrimination results corresponding to the training samples comprises: for each of the nodes, inputting the corresponding time sequence of each of the nodes in the node feature matrix sample into a preset multilayer perceptron for processing to acquire output features; calculating the discrimination result of one node and each of nodes in the incidence node set $N_{real}(v)$ and incidence node set $N_{fake}(v)$ of this one node according to a following formula:

$$D(v_a, v_b) = \sigma(d_{v_a}^T d_{v_b}) = \frac{1}{1 + \exp(-d_{v_a}^T d_{v_b})},$$

where, $D(v_a, v_b)$ represents a discrimination result that a node $v_a$ is an incidence node of a node $v_b$, $d_{v_a}$ represents an output feature of the node $v_a$ and $d_{v_b}$ represents an output feature of the node $v_b$.

Optionally, the loss function is as follows:

$$L(G, D) = \sum_{r=1}^{|V|} \sum_{v_{real} \in N_{real}(v)} \log(D(v_{real}, v_r)) + \sum_{r=1}^{|V|} \sum_{v_{fake} \in N_{fake}(v)} \log(D(v_{fake}, v_r)) + \lambda \|P - T\|_2,$$

where |V| represents the number of the nodes.

In a second aspect, an embodiment of the present application provides a terminal device, which includes: a memory and a processor, where the memory is configured to store a computer program, the processor is configured to execute the method of the first aspect or any embodiment of the first aspect when invoking the computer program.

In a third aspect, an embodiment of the present application provides a computer-readable storage medium on which a computer program is stored, the computer program, when executed by a processor, implements the method of the first aspect or any embodiment of the first aspect.

In a fourth aspect, an embodiment of the present application provides a computer program product, and the computer program product, when running on a processor, causes the processor to implement any method in the first aspect.

It could be understood that, the beneficial effects of the second aspect to the fourth aspect may refer to relevant description in the first aspect, which will not be repeated here again.

EMBODIMENTS OF THE PRESENT APPLICATION

At present, brain atlases are mostly generated based on single-modal image data, which can express less feature information. For example, the structural connection matrix generated based on DTI data can express the structural connection relationship between various brain regions, but cannot express the functional connection relationship between the various brain regions. The node feature matrix generated based on rs-fMRI data can express the functional connection information between the various brain regions, but cannot express the structural connection relationship between the various brain regions. For some chronic neurological brain diseases, such as Alzheimer's disease, pathological characteristics of which are more complex, and it is impossible to accurately reflect disease information from single-modal image data. Therefore, based on the current brain atlases, effective disease information may not be extracted, resulting in misjudgment of the disease diagnosis.

In response to this problem, the present application provides an image-driven brain atlas construction method, which calculates a first hypergraph transition matrix by transforming a node feature matrix into a hypergraph data structure. The first hypergraph transition matrix is a constructed brain atlas.

Among them, the hypergraph is a kind of data structure, which is usually expressed by a hypergraph incidence matrix. In the hypergraph data structure, an edge becomes a hyperedge, which may connect multiple nodes. The hypergraph transition matrix is configured to indicate probability that each node in the hypergraph travels to another node, that is, it may be understood that the hypergraph transition matrix is essentially configured to describe the structural connection relationship between the various nodes in the hypergraph.

The node feature matrix includes time sequences of multiple ROI voxel features of the brain. The so-called time sequence is blood oxygen saturation level data collected at d (d>1, d is an integer) consecutive sampling points by the ROI voxel feature. The node feature matrix may also be called a functional connection matrix, which contains functional connection information among the various ROI voxel features.

Then, when the node feature matrix is transformed into a hypergraph data format, one node in the hypergraph is one ROI voxel feature. The first hypergraph transition matrix calculated based on the node feature matrix may describe the structural connection relationship among the multiple ROI voxel features, and has a certain similarity with the structural connection matrix generated based on the brain DTI data. That is to say, the first hypergraph transition matrix not only includes the functional connection information among the multiple ROI voxel features, but also includes the structural connection relationship among the multiple ROI voxel features.

Therefore, in the present application, through transforming the node feature matrix into the hypergraph data structure and calculating the first hypergraph transition matrix, a multi-modal brain atlas may be constructed. Compared with the current brain connection structures generated based on single-modal image data, this multi-modal brain connection structure can express more feature information, and can improve the accuracy of disease diagnosis when applied to the process of brain disease diagnosis.

The technical solutions of the present application will be described in detail below with specific embodiments. The following specific embodiments may be combined with each other, and the same or similar concepts or processes may not be repeated in some embodiments.

Figure 1:
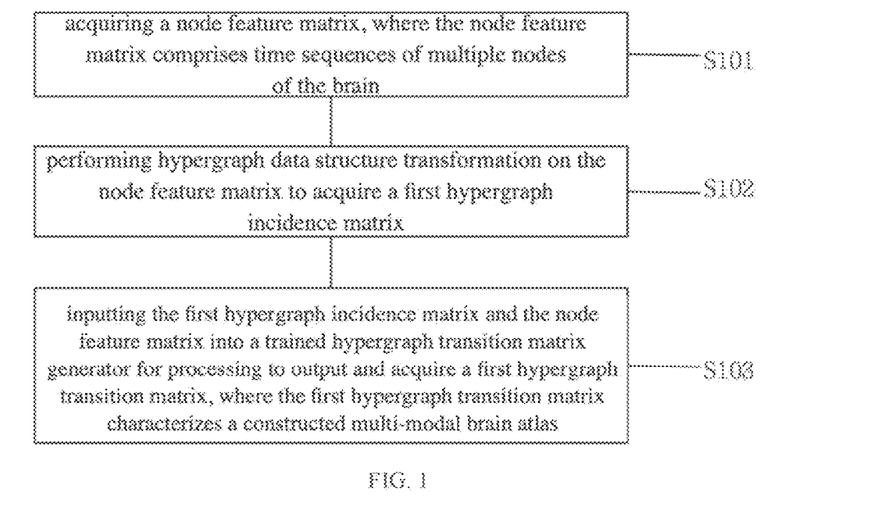
FIG. 1 is a flowchart of an embodiment of an image-driven brain atlas construction method provided by the present application.

As shown in FIG. 1, FIG. 1 is a flowchart of an embodiment of an image-driven brain atlas construction method provided by the present application, an execution subject of this method may be an image data acquisition device, for example, a terminal deice such as a PET (Positron Emission Computed Tomography) device, a CT (Computed Tomography) device, an MRI (Magnetic Resonance Imaging) device, etc. It may also be a terminal device such as a control device of an image data acquisition device, a computer, a robot, a mobile terminal and the like. As shown in FIG. 1, the method includes the following.

At S101, acquire a node feature matrix, where the node feature matrix includes time sequences of multiple nodes of a brain.

Here, the node feature matrix may be generated based on image data of at least one modality. Exemplarily, assuming that an MRI device acquires an image for constructing the node feature matrix is, and image data may include rs-fMRI images, or include MRI images and rs-fMRI images.

For example, after the MRI images and the rs-fMRI images are acquired, DPARSF software and GRETNA software may be used to preprocess the input MRI images and rs-fMRI images, and then preprocessed data may be mapped to AAL (Anatomical Automatic Labeling) templates to obtain the time sequences of multiple ROI voxel features. Among them, one ROI voxel feature is one brain region divided by the AAL template. Hereinafter, the ROI voxel features will be referred to as nodes.

After the time sequences of multiple nodes are acquired, the time sequence of each node is regarded as a column vector, so as to form the node feature matrix $X_V$ of multiple nodes, and $X_V$ is a real matrix of size $|V| \times d$. Among them, $|V|$ represents the number of the nodes, and d represents a time sequence length of the node.

At S102, transforming the node feature matrix into a hypergraph data structure to obtain a first hypergraph incidence matrix.

Exemplarily, in the present application, commonly used methods, such as a K-NN (k-nearest neighbor) classification algorithm, a K-means clustering algorithm etc., can be directly used to perform the conversion of the hypergraph data structure to obtain the first hypergraph incidence matrix.

In one example, the node feature matrix may be first transformed into the first hypergraph data by using a Guth-Katz polynomial clustering algorithm. Namely, the Guth-Katz polynomial clustering algorithm is used to cluster the time sequences in the node feature matrix, and each acquired category may be used as one hyperedge of the first hypergraph data. Each node in the node feature matrix is one node in the first hypergraph data, thereby constructing the first hypergraph data. Then, the KNN algorithm is used to transform the node feature matrix into a second hypergraph data. Finally, the first hypergraph data and the second hypergraph data are fused to obtain the first hypergraph incidence matrix.

In this example, the first hypergraph data is constructed by using the Guth-Katz polynomial clustering algorithm, and then the first hypergraph data is fused with the second hypergraph data to obtain the first hypergraph incidence matrix, such that the topology information among the nodes in the node feature matrix can be better preserved, and redundant interference information is effectively eliminated, thereby improving the accuracy of the first hypergraph incidence matrix.

At S103, input the first hypergraph incidence matrix $A_H$ and the node feature matrix $X_V$ into a trained hypergraph transition matrix generator for processing, and output a first hypergraph transition matrix characterizing a constructed multi-modal brain atlas.

Figure 2:
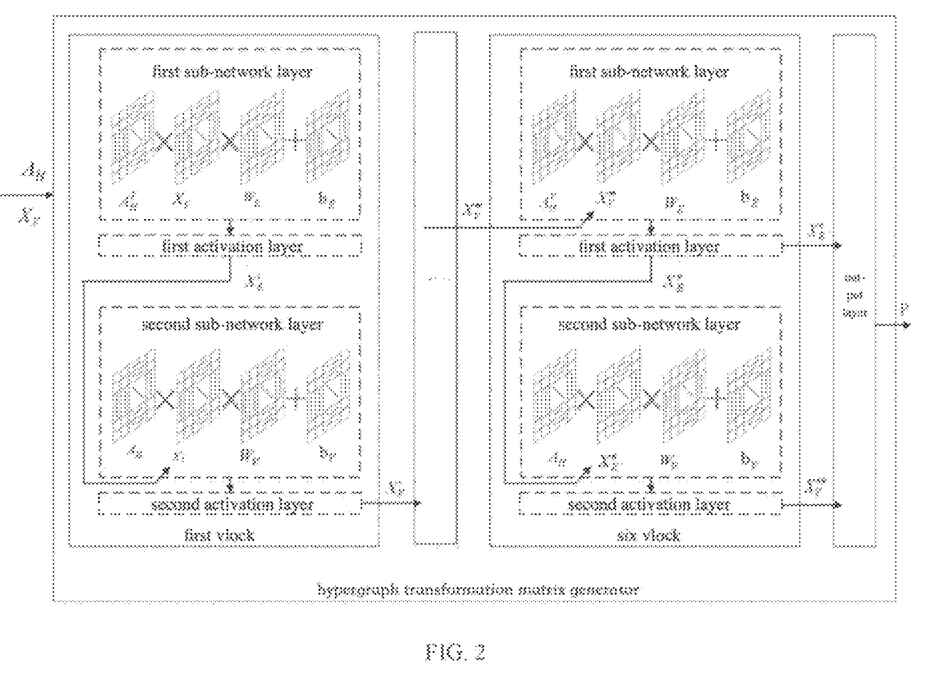
FIG. 2 is a network structure of a hypergraph conversion matrix generator provided by an embodiment of the present application.

As shown in FIG. 2, FIG. 2 is a schematic diagram of a network structure of the hypergraph transition matrix generator provided by the present application, which includes several block layers connected in series and an output layer.

Among them, each of the block layers includes a first sub-network layer, a first activation layer, a second sub-network layer and a second activation layer. The first sub-network layer is a neural network of size d×d, which receives the input node feature matrix $X_V$ for operation, outputs an operation result to the first activation layer, and uses a sigmoid activation function to activate the operation result to obtain a hyperedge feature matrix $X_E'$. Specifically, the expressions of the first sub-network layer and the first activation layer are as follows: $X_E' = \sigma(A_H^T X_V W_E + b_E)$.

Among them, $W_E$ and $b_E$ are network parameters that can be learned in the first sub-network layer, $W_E$ is a weight matrix of size d×d, and $b_E$ is a bias vector of size d×1.

After the first activation layer acquires the hyperedge feature matrix $X_E'$, $X_E'$ will be input to the second sub-network layer. The second sub-network layer is a neural network of size d×d, which receives the input $X_E'$ for operation, outputs an operation result to the second activation layer, and uses a sigmoid activation function to activate the operation result to obtain a new node feature matrix $X_V'$. Specifically, the expressions of the second sub-network layer and the second activation layer are as follows. $X_V' = \sigma(A_H X_E' W_V + b_V)$.

Among them, $W_V$ and $b_V$ are network parameters that can be learned in the second sub-network layer, $W_V$ is a weight matrix of size d×d, and $b_V$ is a bias vector of size d×1.

After the second activation layer acquires the new node feature matrix $X_V'$, $X_V'$ may be output from the block layer where $X_V'$ is located.

It can be understood that several block layers are used to perform several iterative calculations based on the input first hypergraph incidence matrix and node feature matrix to obtain a target hyperedge feature matrix and a target node feature matrix.

For example, six block layers are shown in FIG. 2. Among them, a first block receives $X_V$ from an outside of the hypergraph transition matrix generator, acquires a hyperedge feature matrix $X_E'$ through calculation, calculates a new node feature matrix $X_V'$ by using $X_E'$, and inputs $X_V'$ into a second block. Similarly, after the second block receives $X_V'$, a new $X_E'$ is calculated by using $X_V'$, and a new node feature matrix $X_V''$ is calculated by using $X_E'$, and $X_V''$ is input into a third block. Iterative calculations are performed in turn, a six block serves as the last layer and will use the node feature matrix $X_V'''$ output by the fifth block to calculate a new hyperedge feature matrix $X_E''$, and then uses $X_E''$ to calculate a new node feature matrix $X_V''''$, and then outputs $X_E''$ and $X_V''''$ served as the target hyperedge feature matrix and the target node feature matrix and inputs $X_E''$ and $X_V''''$ to the output layer.

It should be understood that the number of block layers of the hypergraph transition matrix generator is not limited in the present application, and may be set based on actual model performance. Through arranging several block layers and using a hypergraph edge neuron algorithm to alternately learn the hyperedge feature matrix and the node feature matrix, unnecessary parameters can be reduced and model overfitting can be avoided, thereby enhancing the generalization ability of the model.

After receiving the target hyperedge feature matrix $X_E''$ and the target node feature matrix $X_V''''$, the output layer may determine a node weight matrix R according to the first hypergraph incidence matrix $A_H$ and the target node feature matrix $X_V''''$, the expression of which is as follows: R $(X_V''''W_R) \odot A_H$. Where, $W_R$ is a network parameter that can be learned in the output layer, and $W_R$ is a weight matrix with size of $d \times |E|$, where E is the number of hyperedges.

Then the hyperedge weight matrix W is determined according to the target hyperedge feature matrix $X_E''$, the expression of which is as follows: $W = \text{diag}(\vec{a}(X_E'') + \vec{b})$. Where, $\vec{a}$ and $\vec{b}$ are network parameters that can be learned in the output layer, $\vec{a}$ is a d-dimensional vector, and $\vec{b}$ is a $|E|$-dimensional vector.

After that, the calculated hyperedge weight matrix W and node weight matrix R are substituted into the hypergraph transition probability formula to calculate the first hypergraph transition matrix P, the expression of which is as follows: $P = D_V^{-1} W D_E^{-1} R$. Where, $D_V$ represents a vertex degree of freedom and $D_E$ represents a hyperedge degree of freedom.

For the first hypergraph incidence matrix $A_H$, the calculated first hypergraph transition matrix P indicates probability that each of the nodes in the $A_H$ is transited to another node, that is, the first hypergraph transition matrix is essentially used to describe structural connection relationships between the nodes in the $A_H$. Moreover, the nodes in the $A_H$ correspond to the nodes (i.e., the ROI voxel features) indicated by the node feature matrix, therefore, the first hypergraph transition matrix P has a certain similarity with the structural connection matrix generated based on the brain DTI data, which can describe the structural connection relationships between the multiple ROI voxel features. Moreover, the first hypergraph transition matrix P is calculated based on the node feature matrix $X_V$, so the first hypergraph transition matrix P further includes the functional connection information between the multiple ROI voxel features. Then, when the first hypergraph transition matrix P is used as a brain atlas, the brain atlas is a multi-modal brain atlas constructed based on the node feature matrix, and the so-called multi-modality refers to having both the functional connection information and the structural connection information.

After the multi-modal brain atlas is obtained, this brain atlas may be applied to classification and discrimination tasks of any brain disease diagnosed based on medical images.

Exemplarily, a classification network is trained for the AD (Alzheimer's disease), for example, this classification network is a SVM (Support Vector Machine), which predicts probability that a subject develops from mild cognitive impairment into the Alzheimer's disease by inputting the brain atlas. Compared with using the existing brain atlas obtained based on single-modal image data, more disease information can be identified from the multi-modal brain atlas provided in the present application, which can improve the prediction accuracy of the SVM's diagnosis for the Alzheimer's disease.

Figure 3:
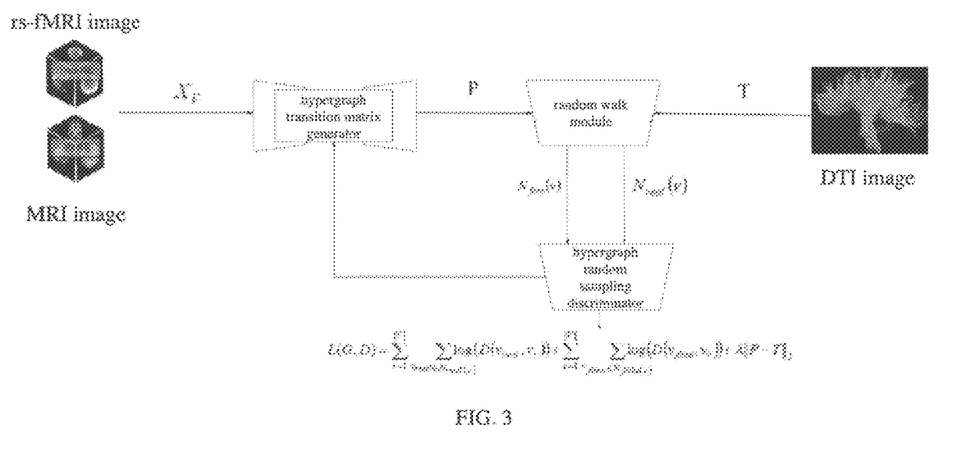
FIG. 3 is a kind of DHGGAN (Dynamic Hyper Graph GAN) provided by an embodiment of the present application.

Regarding the above hypergraph transition matrix generator, the present application further provides a DHGGAN (Dynamic Hyper Graph GAN) to implement the training of the hypergraph transition matrix generator. As shown in FIG. 3, the DHGGAN includes an initial hypergraph transition matrix generator, a random walk module and a hypergraph random sampling discriminator as shown in FIG. 2. The training process may be shown as follows.

At S1, preprocess multi-modal data.

A preset training set includes a plurality of training samples, and each of the training samples includes at least two different modalities of image data samples. Through preprocessing the at least two different modalities of image data samples, node connection matrix samples and structural connection matrix samples are obtained.

Exemplarily, the training samples include rs-fMRI image samples, MRI image samples, and DTI image samples. Through using DPARSF software and GRETNA software to preprocess the input MRI image samples and rs-fMRI image samples first, and then the preprocessed data is mapped to the AAL template to acquire time sequences of multiple nodes v. The time sequence of each of the nodes v is taken as a column vector, so as to constitute the node feature matrix sample of the training samples.

Regarding the DTI image samples, the DTI image samples are input into PANDA software for preprocessing, and the preprocessed data is input into the AAL template to construct the structural connection matrix sample T between the multiple nodes.

At S2, perform hypergraph data structure transformation on the node feature matrix sample to obtain a second hypergraph incidence matrix.

At S3, input the second hypergraph incidence matrix and the node feature matrix sample into the initial hypergraph transition matrix generator for processing to obtain a second hypergraph transition matrix.

The specific processing procedure of the initial hypergraph transition matrix generator for the second hypergraph incidence matrix and the node feature matrix sample may refer to the above S103, which will not be repeated here.

At S4, input the second hypergraph transition matrix P and the structural connection matrix sample T into the random walk module, and determine an incidence node set $N_{real}(v)$ of each node acquired based on the structural connection matrix sample T and an incidence node set $N_{fake}(v)$ of each node acquired based on the second hypergraph transition matrix P.

Exemplarily, walk from $v_0$ to $v_m$ is taken as an example.

Based on the structural connection matrix T, a walk path of walk from $v_0$ to $v_m$ is determined as $(v_1, v_2, \ldots v_{m-1})$. The probability $G_T(v_m|v_0)$ of walk from $v_0$ to $v_m$ is calculated as follows:

$$G_T(v_m|v_0) = \left(\prod_{i=1}^{m} p_T(v_i|v_j)\right) \cdot p_T(v_{m-1}|v_m).$$

Where, $p_T(v_i|v_j)$ represents the probability of walk from the node $v_j$ to the node $v_i$ based on the structural connection matrix T, and the calculation formula of $p_T(v_i|v_j)$ is as follows:

$$p_T(v_i \mid v_j) = \frac{\exp(T_{i,j})}{\sum_{k=1}^{|V|} \exp(T_{k,j})}.$$

Based on the second hypergraph transition matrix P, the walk path of walk from $v_0$ to $v_m$ is determined as $(v_1, v_2, \ldots v_{m-1})$. The probability $G_H(v_m|v_0)$ of walk from $v_0$ to $v_m$ as follows:

$$G_H(v_m \mid v_0) = \left(\prod_{i=1}^{m} p_P(v_i \mid v_j)\right) \cdot p_P(v_{m-1} \mid v_m).$$

Where, $p_P(v_i|v_j)$ represents the probability of walk from the node $v_j$ to the node $v_i$ based on the structural connection matrix P, and the calculation formula of $p_P(v_i|v_j)$ is as follows:

$$p_P(v_i \mid v_j) = \frac{\exp(T_{i,j})}{\sum_{k=1}^{|V|} \exp(T_{k,j})}.$$

Regarding each node $v_r$ in the graph, according to the above calculation method of the random walk probability, n (n≥1, n is an integer) nodes sampled based on the structural connection matrix T and provided with the largest walk probability serve as incidence nodes which are denoted as $N_{real}(v)$. n nodes sampled based on the second hypergraph transition matrix P and provided with the largest walk probability serve as incidence nodes which are denoted as $N_{fake}(v)$.

At S5, input the node incidence sets $N_{real}(v)$ and $N_{fake}(v)$ of each node into the hypergraph random sampling discriminator for discrimination.

Exemplarily, the hypergraph random sampling discriminator may include a multi-layer perceptron indicated by M. For each node $v_r$, the corresponding time sequence $X_{v_r}$ in the node feature matrix sample $X_V$ is input as feature information into the multi-layer perceptron indicated by M for processing to obtain an output feature $d_{v_r} = M(X_{v_r})$.

For any two nodes $v_a$ and $v_b$, the probability $D(v_a, v_b)$ that $v_a$ is an incidence node of $v_b$ may be determined according to the following formula.

$$D(v_a, v_b) = \sigma(d_{v_a}^T d_{v_b}) = \frac{1}{1 + \exp(-d_{v_a}^T d_{v_b})}.$$

For each node $v_r$, the probability that each node in this node's incidence node sets $N_{real}(v)$ and $N_{fake}(v)$ is an incidence node of this node is calculated based on the above formula to obtain a discrimination result.

At S6, calculate model loss based on the discrimination result of the hypergraph random sampling discriminator.

The discrimination result is substituted into the following loss function to calculate a loss value of the DHGGAN model:

$$L(G,D) = \sum_{r=1}^{|V|} \sum_{v_{real} \in N_{real}(v)} \log(D(v_{real}, v_r)) +$$

$$\sum_{r=1}^{|V|} \sum_{v_{fake} \in N_{fake}(v)} \log(D(v_{fake}, v_r)) + \lambda \|P - T\|_2.$$

If the calculated loss value L(G,D) does not meet a preset condition, then the network parameters in the discriminator and the hypergraph transition matrix generator are modified, such as $W_E$, $b_E$, $W_V$, $b_V$ in each block layer and $W_R$, $\vec{a}$, $\vec{b}$ etc. in the output layer. Then new training samples are selected, the S2 is restarted, and the next round of training is started until the model converges, that is, the calculated loss value L(G,D) meets the preset condition. The preset condition may be that the loss value tends to level off.

It is worth noting that, based on the convergence condition of the model, $W_E$, $b_E$, $W_V$ and $b_V$ in different block layers may be adjusted to be different or the same parameters eventually. Moreover, as the model converges, the second hypergraph transition matrix P becomes more and more similar to the structural connection matrix T. That is to say, after the training is completed, the hypergraph transition matrix generator may generate the first hypergraph transition matrix that has a certain degree of similarity with the actual structural connection matrix based on the node feature matrix, so that when the first hypergraph transition matrix is used as a brain atlas, this brain atlas has both functional connection information, structural connection information, and complementary information between the functional connection information and the structural connection information, which can provide more feature information and improve efficiency of subsequent disease diagnosis.

In the embodiments of the present application, the random walk principle on the hypergraph is used to replace the kernel function transformation and the Lagrange multiplier method in the traditional training method, thereby avoiding the complicated calculation in the non-convex optimization problem and avoiding the problem that the loss function can not stably converge toward a global optimal point, therefore, the robustness as well as the training efficiency of the model are improved.

Based on the same inventive concept, as an implementation of the above method, an embodiment of the present application provides an image-driven brain atlas construction apparatus, and this apparatus embodiment corresponds to the foregoing method embodiments. In order to facilitate reading, the details in the foregoing method embodiments are not described one by one in this apparatus embodiment any more, but it should be clear that the apparatus in this embodiment can correspondingly implement all the content in the foregoing method embodiments.

Figure 4:
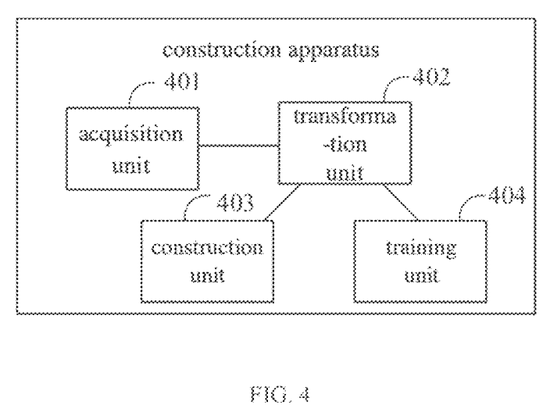
FIG. 4 is a structural schematic diagram of an image-driven brain atlas construction apparatus provided by an embodiment of the present application.

FIG. 4 is a structural schematic diagram of an image-driven brain atlas construction apparatus provided by an embodiment of the present application. As shown in FIG. 4, the construction apparatus provided by this embodiment includes an acquisition unit 401, a conversion unit 402, and a construction unit 403.

Among them, the acquisition unit 401 is configured to acquire a node feature matrix including time sequences of multiple nodes of a brain.

The conversion unit 402 is configured to perform hypergraph data structure transformation on the node feature matrix to obtain a first hypergraph incidence matrix.

The construction unit 403 is configured to input the first hypergraph incidence matrix and the node feature matrix into a trained hypergraph transition matrix generator for processing to output and acquire a first hypergraph transition matrix characterizing a constructed multi-modal brain atlas.

Optionally, the acquisition unit 401 is further configured to preprocess training samples for each of the training samples in a training set to acquire a node feature matrix sample and a structural connection matrix sample.

The conversion unit 402 is further configured to perform hypergraph data structure transformation on the node feature matrix sample to obtain a second hypergraph incidence matrix.

The construction apparatus further includes a training unit 404 configured to: input the second hypergraph incidence matrix and the node feature matrix sample into an initial hypergraph transition matrix generator for processing to output and acquire a second hypergraph transition matrix; based on a random walk principle on a hypergraph, determine an incidence node set $N_{real}(v)$ acquired based on the structural connection matrix sample and an incidence node set $N_{fake}$ acquired based on the second hypergraph transition matrix for each of nodes corresponding to the training samples; use a discriminator to discriminate $N_{real}(v)$ and $N_{fake}(v)$ of each of the nodes to acquire discrimination results corresponding to the training samples; perform iterative training according to the discrimination result corresponding to each of the training samples and a preset loss function to acquire the hypergraph transition matrix generator.

The construction apparatus provided in this embodiment can execute the above method embodiments, and their implementation principles and technical effects are similar, and details of which are not described herein again.

Those skilled in the art can clearly understand that, for the convenience and simplicity of description, the division of the above-mentioned functional units and modules is only used as an example for illustration. In practical applications, the above-mentioned functions can be allocated to different functional units or module for completion according to needs, that is, the internal structure of the apparatus is divided into different functional units or modules to complete all or part of the functions described above. Each functional unit or module in the embodiments may be integrated in one processing unit, or each unit may exist physically alone, or two or more units may be integrated into one unit, and the above-mentioned integrated unit may be implemented in a form of hardware or in a form of software functional unit. In addition, the specific names of the functional units and modules are only for the convenience of distinguishing each other, and are not used to limit the protection scope of the present application. For the specific working processes of the units and modules in the above-mentioned system, reference may be made to the corresponding processes in the foregoing method embodiments, which will not be repeated herein again.

Figure 5:
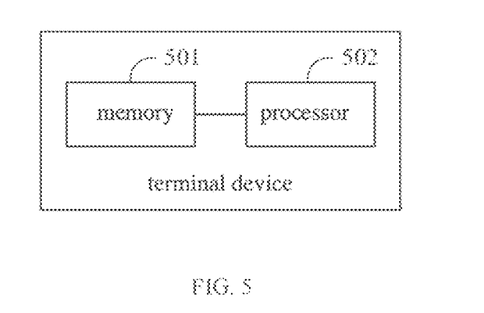
FIG. 5 is a structural schematic diagram of a terminal device provided by an embodiment of the present application.

Based on the same inventive concept, an embodiment of the present application further provides a terminal device. FIG. 5 is a structural schematic diagram of a terminal device provided by an embodiment of the present application. As shown in FIG. 5, the terminal device provided by this embodiment includes: a memory 501 and a processor 502, where the memory 501 is configured to store a computer program; the processor 502 is configured to implement the methods described in the above method embodiments when invoking the computer program.

The terminal device provided in this embodiment may implement the foregoing method embodiments, and their implementation principles and technical effects are similar, and details of which are not described herein again.

Embodiments of the present application further provide a computer-readable storage medium on which a computer program is stored, and the computer program, when executed by a processor, realizes the methods described in the foregoing method embodiments.

Embodiments of the present application further provide a computer program product, when the computer program product runs on a terminal device, the computer program product causes the terminal device to execute and implement the methods described in the foregoing method embodiments.

If the above-mentioned integrated unit is implemented in the form of software functional unit and sold or used as an independent product, it may be stored in a computer-readable storage medium. Based on this understanding, all or part of the processes in the methods of the above embodiments can be implemented through instructing relevant hardware by a computer program, and the computer program may be stored in the computer-readable storage medium, and the computer program, when executed by a processor, may implements the steps of each of the above method embodiments. Here, the computer program includes a computer program code, and the computer program code may be in a form of a source code, an object code, an executable file or some intermediate form, and the like. The computer-readable storage medium may include at least: any entity or apparatus capable of carrying the computer program code to a photographing apparatus/terminal device, recording medium, computer memory, ROM (Read-Only Memory), RAM (Random Access Memory), electrical carrier signal, telecommunication signal and software distribution medium. For example, a U disk, a mobile hard disk, a magnetic disk or a CD, etc. In some jurisdictions, according to legislation and patent practice, the computer-readable medium can not be the electrical carrier signal and telecommunications signal.

In the foregoing embodiments, the description for each embodiment has its own emphasis. For parts that are not described or described in detail in a certain embodiment, reference may be made to the relevant descriptions of other embodiments.

Those of ordinary skill in the art should realize that the units and algorithm steps of each example described in conjunction with the embodiments disclosed herein may be implemented by electronic hardware, or a combination of computer software and electronic hardware. Whether these functions are performed by hardware or software depends on specific applications and design constraints of the technical solution. Those skilled in the art may implement the described functions by using different methods for each particular application, but such implementations should not be considered beyond the scope of the present application.

In the embodiments provided in the present application, it should be understood that the disclosed apparatus/device and method may be implemented in other manners. For example, the apparatus/device embodiments described above are only illustrative. For example, the division of the modules or units is only a logical function division, and there may be other division methods in actual implementations, for example, multiple units or components may be combined or may be integrated into another system, or some features may be omitted or not implemented. On another perspective, the shown or discussed mutual coupling or direct coupling or communication connection may be indirect coupling or communication connection of devices or units through some interfaces, and may be in an electrical form, a mechanical form or other forms.

It should be understood that, when used in this specification and the appended claims of the present application, the term "comprising" indicates the presence of the described feature, entity, step, operation, element and/or component, but does not exclude the presence or addition of one or more other features, entities, steps, operations, elements, components and/or sets thereof.

It should also be understood that, the term "and/or" used in this specification and the appended claims of the present application refers to any combination and all possible combinations of one or more of the associated listed items, and includes these combinations.

As used in this specification and the appended claims of the present application, the term "if" may be contextually interpreted as "when" or "once" or "in response to determination of . . . " or "in response to detection of . . . ". Similarly, the phrases "if . . . is determined" or "if [the described condition or event] is detected" may be contextually interpreted to mean "once . . . is determined" or "in response to determination of . . . " or "once [the described condition or event] is detected]" or "in response to detection of [the described condition or event]".

In addition, in the description of this specification and the appended claims of the present application, the terms "first", "second", "third", etc. are only used to distinguish the description, and should not be construed as indication or implication of relative importance.

References in this specification of the present application to "one embodiment" or "some embodiments" and the like mean that one or more embodiments of the present application include a particular feature, structure or characteristic described in connection with this embodiment. Thus, the phrases "in one embodiment," "in some embodiments," "in some other embodiments," "in other embodiments," etc. appeared at different places of this specification are not necessarily all refer to the same embodiment, but mean "one or more but not all embodiments", unless additionally and specifically emphasized otherwise. The terms "including", "comprising", "having" and variations thereof mean "including but being not limited to", unless additionally and specifically emphasized otherwise.

Finally, it should be noted that the above embodiments are only used to illustrate, but not to limit, the technical solutions of the present application; although the present application has been described in detail with reference to the foregoing embodiments, those of ordinary skill in the art should understand that: they can still modify the technical solutions described in the foregoing embodiments, or equivalently replace some or all of the technical features in the technical solutions described in the foregoing embodiments; and these modifications or replacements do not make the essence of the corresponding technical solutions deviate from the scope of the technical solutions of the embodiments of the present application.

What is claimed is:

1. An image-driven brain atlas construction method, comprising:

acquiring a node feature matrix, wherein the node feature matrix comprises time sequences of multiple nodes of a brain;

performing hypergraph data structure transformation on the node feature matrix to acquire a first hypergraph incidence matrix;

inputting the first hypergraph incidence matrix and the node feature matrix into a trained hypergraph transition matrix generator for processing to output and acquire a first hypergraph transition matrix, wherein the first hypergraph transition matrix characterizes a constructed multi-modal brain atlas;

wherein the performing hypergraph data structure transformation on the node feature matrix to acquire the first hypergraph incidence matrix comprises:

transforming the node feature matrix into first hypergraph data by using a Guth-Katz polynomial clustering algorithm;

transforming the node feature matrix into second hypergraph data by using a KNN algorithm;

fusing the first hypergraph data and the second hypergraph data to acquire the first hypergraph incidence matrix.

2. The method of claim 1, wherein the processing of the node feature matrix by the hypergraph transition matrix generator comprises:

performing several iterative calculations based on the first hypergraph incidence matrix and the node feature matrix to obtain a target hyperedge feature matrix and a target node feature matrix;

determining a node weight matrix according to the first hypergraph incidence matrix and the target node feature matrix;

determining a hyperedge weight matrix according to the target hyperedge feature matrix;

determining the first hypergraph transition matrix according to the hyperedge weight matrix and the node weight matrix.

3. The method of claim 1, wherein the method further comprises:

preprocessing each of training samples in a training set to acquire a node feature matrix sample and a structural connection matrix sample;

performing hypergraph data structure transformation on the node feature matrix sample to acquire a second hypergraph incidence matrix;

inputting the second hypergraph incidence matrix and the node feature matrix sample into an initial hypergraph transition matrix generator for processing to output and acquire a second hypergraph transition matrix;

based on a random walk principle on a hypergraph, determining an incidence node set $N_{real}(v)$ acquired based on the structural connection matrix sample and an incidence node set $N_{fake}(v)$ acquired based on the second hypergraph transition matrix for each of the nodes corresponding to the training samples;

performing discrimination on the incidence node set $N_{real}(v)$ and the incidence node set $N_{fake}(v)$ of each of the nodes by using a discriminator to acquire discrimination results corresponding to the training samples;

performing iterative training according to the discrimination result corresponding to each of the training samples and a preset loss function to acquire the hypergraph transition matrix generator.

4. The method of claim 3, wherein, the performing discrimination on the incidence node set $N_{real}(v)$ and the incidence node set $N_{fake}(v)$ of each of the nodes by using a discriminator to acquire discrimination results corresponding to the training samples comprises:

for each of the nodes, inputting the corresponding time sequence of each of the nodes in the node feature matrix sample into a preset multilayer perceptron for processing to acquire output features;

calculating the discrimination result of one node and each of nodes in the incidence node set $N_{real}(v)$ and incidence node set $N_{fake}(v)$ of this one node according to a following formula:

$$D(v_a, v_b) = \sigma(d_{v_a}^T d_{v_b}) = \frac{1}{1 + \exp(-d_{v_a}^T d_{v_b})},$$

where, $D(v_a, v_b)$ represents a discrimination result that a node $v_a$ is an incidence node of a node $v_b$, $d_{v_a}$ represents an output feature of the node $v_a$, and $d_{v_b}$ represents an output feature of the node $v_b$.

5. The method of claim 4, wherein the loss function is as follows:

$$L(G, D) = \sum_{r=1}^{|V|} \sum_{v_{real} \in N_{real}(v)} \log(D(v_{real}, v_r)) +$$

$$\sum_{r=1}^{|V|} \sum_{v_{fake} \in N_{fake}(v)} \log(D(v_{fake}, v_r)) + \lambda \|P - T\|_2,$$

where $|V|$ represents the number of the nodes.

6. A terminal device, comprising: a memory and a processor, wherein the memory is configured to store a computer program, the processor, when invoking the computer program, is configured to execute:

acquiring a node feature matrix, wherein the node feature matrix comprises time sequences of multiple nodes of a brain;

performing hypergraph data structure transformation on the node feature matrix to acquire a first hypergraph incidence matrix;

inputting the first hypergraph incidence matrix and the node feature matrix into a trained hypergraph transition matrix generator for processing to output and acquire a first hypergraph transition matrix, wherein the first hypergraph transition matrix characterizes a constructed multi-modal brain atlas;

wherein the performing hypergraph data structure transformation on the node feature matrix to acquire the first hypergraph incidence matrix comprises:

transforming the node feature matrix into first hypergraph data by using a Guth-Katz polynomial clustering algorithm;

transforming the node feature matrix into second hypergraph data by using a KNN algorithm;

fusing the first hypergraph data and the second hypergraph data to acquire the first hypergraph incidence matrix.

7. A non-transitory computer-readable storage medium on which a computer program is stored, wherein the computer program, when executed by a processor, implements:

acquiring a node feature matrix, wherein the node feature matrix comprises time sequences of multiple nodes of a brain;

performing hypergraph data structure transformation on the node feature matrix to acquire a first hypergraph incidence matrix;

inputting the first hypergraph incidence matrix and the node feature matrix into a trained hypergraph transition matrix generator for processing to output and acquire a first hypergraph transition matrix, wherein the first hypergraph transition matrix characterizes a constructed multi-modal brain atlas;

the performing hypergraph data structure transformation on the node feature matrix to acquire the first hypergraph incidence matrix comprises:

transforming the node feature matrix into first hypergraph data by using a Guth-Katz polynomial clustering algorithm;

transforming the node feature matrix into second hypergraph data by using a KNN algorithm;

fusing the first hypergraph data and the second hypergraph data to acquire the first hypergraph incidence matrix.

8. The terminal device of claim 6, wherein the processing of the node feature matrix by the hypergraph transition matrix generator comprises:

performing several iterative calculations based on the first hypergraph incidence matrix and the node feature matrix to obtain a target hyperedge feature matrix and a target node feature matrix;

determining a node weight matrix according to the first hypergraph incidence matrix and the target node feature matrix;

determining a hyperedge weight matrix according to the target hyperedge feature matrix;

determining the first hypergraph transition matrix according to the hyperedge weight matrix and the node weight matrix.

9. The terminal device of claim 6, wherein the processor, when invoking the computer program, is further configured to execute:

preprocessing each of training samples in a training set to acquire a node feature matrix sample and a structural connection matrix sample;

performing hypergraph data structure transformation on the node feature matrix sample to acquire a second hypergraph incidence matrix;

inputting the second hypergraph incidence matrix and the node feature matrix sample into an initial hypergraph transition matrix generator for processing to output and acquire a second hypergraph transition matrix;

based on a random walk principle on a hypergraph, determining an incidence node set $N_{real}(v)$ acquired based on the structural connection matrix sample and an incidence node set $N_{fake}(v)$ acquired based on the second hypergraph transition matrix for each of the nodes corresponding to the training samples;

performing discrimination on the incidence node set $N_{real}(v)$ and the incidence node set $N_{fake}(v)$ of each of the nodes by using a discriminator to acquire discrimination results corresponding to the training samples;

performing iterative training according to the discrimination result corresponding to each of the training samples and a preset loss function to acquire the hypergraph transition matrix generator.

10. The terminal device of claim 9, wherein, the performing discrimination on the incidence node set $N_{real}(v)$ and the incidence node set $N_{fake}(v)$ of each of the nodes by using a discriminator to acquire discrimination results corresponding to the training samples comprises:

for each of the nodes, inputting the corresponding time sequence of each of the nodes in the node feature matrix sample into a preset multilayer perceptron for processing to acquire output features;

calculating the discrimination result of one node and each of nodes in the incidence node set $N_{real}(v)$ and incidence node set $N_{fake}(v)$ of this one node according to a following formula:

$$D(v_a, v_b) = \sigma(d_{v_a}^T d_{v_b}) = \frac{1}{1 + \exp(-d_{v_a}^T d_{v_b})},$$

where, $D(v_a, v_b)$ represents a discrimination result that a node $v_a$ is an incidence node of a node $v_b$, $d_{v_a}$ represents an output feature of the node $v_a$, and $d_{v_b}$ represents an output feature of the node $v_b$.

11. The terminal device of claim 10, wherein the loss function is as follows:

$$L(G, D) = \sum_{r=1}^{|V|} \sum_{v_{real} \in N_{real}(v)} \log(D(v_{real}, v_r)) +$$

$$\sum_{r=1}^{|V|} \sum_{v_{fake} \in N_{fake}(v)} \log(D(v_{fake}, v_r)) + \lambda \|P - T\|_2,$$

where $|V|$ represents the number of the nodes.

12. The non-transitory computer-readable storage medium of claim 7, wherein the processing of the node feature matrix by the hypergraph transition matrix generator comprises:
   performing several iterative calculations based on the first hypergraph incidence matrix and the node feature matrix to obtain a target hyperedge feature matrix and a target node feature matrix;
   determining a node weight matrix according to the first hypergraph incidence matrix and the target node feature matrix;
   determining a hyperedge weight matrix according to the target hyperedge feature matrix;
   determining the first hypergraph transition matrix according to the hyperedge weight matrix and the node weight matrix.

13. The non-transitory computer-readable storage medium of claim 7, wherein the computer program, when executed by a processor, further implements:
   preprocessing each of training samples in a training set to acquire a node feature matrix sample and a structural connection matrix sample;
   performing hypergraph data structure transformation on the node feature matrix sample to acquire a second hypergraph incidence matrix;
   inputting the second hypergraph incidence matrix and the node feature matrix sample into an initial hypergraph transition matrix generator for processing to output and acquire a second hypergraph transition matrix;
   based on a random walk principle on a hypergraph, determining an incidence node set $N_{real}(v)$ acquired based on the structural connection matrix sample and an incidence node set $N_{fake}(v)$ acquired based on the second hypergraph transition matrix for each of the nodes corresponding to the training samples;
   performing discrimination on the incidence node set $N_{real}(v)$ and the incidence node set $N_{fake}(v)$ of each of the nodes by using a discriminator to acquire discrimination results corresponding to the training samples;
   performing iterative training according to the discrimination result corresponding to each of the training samples and a preset loss function to acquire the hypergraph transition matrix generator.

14. The non-transitory computer-readable storage medium of claim 13, wherein,
   the performing discrimination on the incidence node set $N_{real}(v)$ and the incidence node set $N_{fake}(v)$ of each of the nodes by using a discriminator to acquire discrimination results corresponding to the training samples comprises:
   for each of the nodes, inputting the corresponding time sequence of each of the nodes in the node feature matrix sample into a preset multilayer perceptron for processing to acquire output features;
   calculating the discrimination result of one node and each of nodes in the incidence node set $N_{real}(v)$ and incidence node set $N_{fake}(v)$ of this one node according to a following formula:

$$D(v_a, v_b) = \sigma(d_{v_a}^T d_{v_b}) = \frac{1}{1 + \exp(-d_{v_a}^T d_{v_b})},$$

where, $D(v_a, v_b)$ represents a discrimination result that a node $v_a$ is an incidence node of a node $v_b$, $d_{v_a}$ represents an output feature of the node $v_a$, and $d_{v_b}$ represents an output feature of the node $v_b$.

15. The non-transitory computer-readable storage medium of claim 14, wherein the loss function is as follows:

$$L(G, D) = \sum_{r=1}^{|V|} \sum_{v_{real} \in N_{real}(v)} \log(D(v_{real}, v_r)) +$$

$$\sum_{r=1}^{|V|} \sum_{v_{fake} \in N_{fake}(v)} \log(D(v_{fake}, v_r)) + \lambda \|P - T\|_2, \text{ where } |V|$$

where $|V|$ represents the number of the nodes.

* * * * *